US009314495B2

(12) United States Patent
Tewari et al.

(10) Patent No.: US 9,314,495 B2
(45) Date of Patent: Apr. 19, 2016

(54) PROCESS FOR PYGEUM EXTRACTION

(76) Inventors: Kiran Tewari, Panchkula (IN); Ashok Sharma, Panchkula (IN)

( * ) Notice: Subject to any disclaimer, the term of this patent is extended or adjusted under 35 U.S.C. 154(b) by 419 days.

(21) Appl. No.: 13/877,164

(22) PCT Filed: Jul. 19, 2012

(86) PCT No.: PCT/IN2012/000508
§ 371 (c)(1),
(2), (4) Date: Mar. 30, 2013

(87) PCT Pub. No.: WO2013/014681
PCT Pub. Date: Jan. 31, 2013

(65) Prior Publication Data
US 2013/0236574 A1    Sep. 12, 2013

(30) Foreign Application Priority Data

Jul. 22, 2011  (IN) .......................... 2068/DEL/2011

(51) Int. Cl.
*A61K 36/736* (2006.01)
*A23L 1/30* (2006.01)
*A23L 2/52* (2006.01)

(52) U.S. Cl.
CPC .............. *A61K 36/736* (2013.01); *A23L 1/3002* (2013.01); *A23L 2/52* (2013.01); *A61K 2236/00* (2013.01)

(58) Field of Classification Search
USPC .......................................... 424/725, 769, 735
IPC ..................................................... A61K 36/736
See application file for complete search history.

(56) References Cited

U.S. PATENT DOCUMENTS

| | | | |
|---|---|---|---|
| 3,856,946 A | 12/1974 | Debat | |
| 4,258,037 A * | 3/1981 | Juvin | 424/735 |
| 6,399,115 B2 * | 6/2002 | Revel | 424/727 |
| 6,607,755 B2 * | 8/2003 | Farley | 424/735 |
| 6,790,464 B2 * | 9/2004 | Kuok et al. | 424/725 |
| 7,700,654 B2 * | 4/2010 | Hoffmann et al. | 514/604 |
| 2002/0001632 A1 * | 1/2002 | Revel | 424/727 |
| 2002/0001633 A1 * | 1/2002 | Revel | 424/727 |
| 2003/0099728 A1 * | 5/2003 | Farley | 424/735 |
| 2009/0123564 A1 * | 5/2009 | Jain et al. | 424/642 |
| 2009/0143466 A1 * | 6/2009 | Hoffmann et al. | 514/544 |
| 2012/0077994 A1 * | 3/2012 | Hoerl et al. | 549/406 |
| 2014/0309294 A1 * | 10/2014 | Erfurt et al. | 514/456 |

FOREIGN PATENT DOCUMENTS

WO    WO 2009/135352    * 11/2009

OTHER PUBLICATIONS

Stewart, K. J. Ethnopharmacol. 2003. vol. 89, pp. 3-13.*
Website document from the New World Encyclopedia entitled "Prunus". 2008. 6-pages. website: http://www.new-worldencyclopedia.org/entry/Prunus.*
Swaroop et al. FASEB Journal. Apr. 2015. vol. 29, No. 1, Supp. Meeting Abstracts. 1-page EMBASE Abstract enclosed.*
International Search Report, Oct. 17, 2012, from International Phase of the instant application.

* cited by examiner

*Primary Examiner* — Chris R Tate
(74) *Attorney, Agent, or Firm* — Ladas & Parry LLP

(57) ABSTRACT

An improved process for the extraction of *pygeum* from the plant of the family rosacaea, amygdales tribe, genus *Prunus* species *domestica* (*Indian Prunus*) and related species (as herein defined) comprising the steps of collecting the plant material i.e. stem cuttings/twigs, removing the leaves and drying till moisture content is about 10-15%, powdering the stem material, extracting with chlorinated organic solvents and water-alcohol mixture, in ratio of 1:4, filtering and drying the extract under vacuum at 30 degree Celsius to obtain a greenish mass with bitter almond smell, the mass being referred to as '*pygeum*' wherein in the improved process, a 'renewable plant source' i.e. stem cuttings/twigs, are used for extraction of *pygeum* instead of a 'non-renewable' source such as bark of the tree. The *pygeum* obtained by the new process has a pharmacopeia profile similar to the product '*pygeum*' obtained from a 'non-renewable source' i.e. bark of *Pygeum africanum*. Further, it is non-toxic and shows anti-BPH (benign prostatic hyperplasia) activity comparable with that of *pygeum* obtained from non-renewable source i.e. bark of *Prunus africana*.

2 Claims, No Drawings

PROCESS FOR PYGEUM EXTRACTION

FIELD OF INVENTION

The present invention relates to the field of phyto-chemistry (plant chemistry). More specifically, it relates to a novel, innovative, eco-friendly process for the extraction of a bioactive substance "*pygeum*" from the plants of the *prunus* family, using a 'renewable source'—'pruning material' or 'twigs' instead of a 'non-renewable source' i.e. bark.

BACKGROUND OF THE INVENTION

Definitions

*Pygeum*: Pygeum is the soft gummy mass extracted from the bark of *Prunus africana* tree also called "African plum tree". Wherever used in this patent application, the word *pygeum* refers to the herbal extract obtained by extraction from the plant source material i.e. *Prunus africana* or *Prunus domestica* (*Indian Plum*). In case the word '*pygeum*' is being used in the context of the plant alone and not the extract, same is duly elaborated.

Renewable plant source: Refers to a source which gets naturally renewed e.g. leaves, flowers, seeds, stem cuttings or prunes. Since plant remains alive, the sources keep on getting 'renewed'.

Non-renewable plant source: Refers to a source which if used results in death of plant e.g. root, barks. Since the plant dies, the source does not get renewed.

Pruned stem cuttings/twigs: These are small shoots or branches (about six inches to eighteen inches) obtained as a plant waste during the 'pruning' or trimming process in which superfluous branches are cut to promote good growth and fruiting in the plant. It is a regular activity/process which is carried out to ensure healthy growth of plants and good fruiting.

Analytically defined extract or chemically defined extract: It refers to an extract from a natural source, in which the content of the active ingredients is determined by modern analytical/scientific methods as per pharmacopeia standards.

PAE (*Pygeum africanum* extract): It is the chemically defined extract obtained from the bark of *Prunus africana*. Since it is obtained from the *Prunus* tree of '*africana*' species, the *pygeum* extract obtained is called '*pygeum africanum* extract' also.

Source of *Pygeum*

*Pygeum* is an extract (gummy mass) obtained from the bark of *Prunus africana*. The *Prunus africana* tree is an evergreen tree native to African forest regions and can grow to approximately 45 m in height. The plant belongs to the family rosacaea, tribe amygdales, genus *Prunus* and species *africana*. The leaves are thick and oblong in shape; the flowers are small and white. *Pygeum* fruit is a red berry, resembling a cherry when ripe. The bark (red, brown, or gray) is the part of the plant used for medicinal purposes. Related species are *Prunus domestica* (Hook) F. Kalkm or *Pygeum stricasla* (Hook) and also includes *Prunus Latifolium, Prunus parviforum, Prunus crassifolluni, Prunus lusitanica* and *Primus laurocerasus*.

Clinical Importance of *Pygeum*

*Pygeum* has clinical importance. It has been used for several decades for the treatment and prevention of enlarged prostate (benign prostatic hyperplasia or BPH). The active ingredient in *pygeum* is beta sitosterol. Powdered bark of the *pygeum* tree had been used by African natives to treat urinary problems. In modern times, rather than simply using the 'powdered bark' (which faces challenges of lack of standardization), focus is on use of 'analytically defined extract' from the *pygeum* tree i.e. *Prunus africana* (also called *Pygeum africanum* since this tree is the source of '*pygeum*'). As per online information (http://www.drugs.com/npc/pygeum-.html) *pygeum* has been used to:
- improve symptoms of benign prostatic hypertrophy (BPH) and
- to improve sexual function.

In France, *Pygeum africanum* extract (PAE) has become the primary course of treatment for enlarged prostate. In contrast, surgery is the main option in other Western countries.

*Pygeum* is also therapeutic:
- as an anti-inflammatory
- to increase prostatic secretions and
- to decrease certain hormones in the glandular area, which reduces the hypertrophy (swelling).
- other actions of *pygeum* include increase in bladder elasticity and cell modifications.
- PAE's "phyto-estrogenic" action markedly reduces prostatic hypertrophy. Most trial results report improvement of BPH (Benign Prostatic Hyperplasia) symptoms. When compared with saw palmetto in a clinical trial, it was demonstrated that saw palmetto produced greater reduction of symptoms and was better tolerated. However, PAE may have greater effects on prostate secretion. By improving an underlying problem, PAE may improve sexual function. *Pygeum* clinical trials (mostly European) are encouraging, but more research is needed in the US.

*Pygeum* alone has been shown in some double-blind trials to help men with BPH by improving urinary flow and other symptoms of BPH. It has also been used successfully in combination with nettle root to treat BPH. Long-term BPH studies (six months or greater) on *pygeum* are however lacking. A wealth of literature is available in the prior art on the usefulness of *pygeum* in the management/treatment of enlarged prostate.

Some selected references on clinical importance of *pygeum* are listed below:

1. Andro M C, Riffaud J P. *Pygeum africanum* extract for the treatment of patients with benign prostatic hyperplasia: a review of 25 years of published experience. *Curr Ther Res* 1995; 56:796-817.
2. Carani C, Salvioli V, Scuteri A, et al. Urological and sexual evaluation of treatment of benign prostatic disease using *Pygeum africanum* at high doses. *Arch Ital Urol Nefrol Androl* 1991; 63:341-5 [in Italian].
3. Menchini-Fabris G F, Giorgi P, Andreini F, et al. New perspectives on treatment of prostato-vesicular pathologies with *Pygeum Africanum. Arch It Urol* 1988; LX: 313-22 [in Italian].
4. Murray M T. The Healing Power of Herbs. Rocklin, Calif.: Prima Publ. 1995, 286-93.
5. Barlet A, Albrecht J, Aubert A, et al. Efficacy of *Pygeum africanum* extract in the treatment of micturational disorders due to benign prostatic hyperplasia. Evaluation of objective and subjective parameters. A multicenter, randomized, double-blind trial. *Wein Klin Wochenschr* 1990; 102:667-73.
6. Krzeski T, Kazón M Borkowski A, et al. Combined extracts of *Urtica dioica* and *Pygeum africanum* in the treatment of benign prostatic hyperplasia: Double-blind comparison of two doses. *Clin Ther* 1993; 15:1011-20.
7. Chatelain C, Autet W, Brackman F. Comparison of once and twice daily dosage forms of *Pygeum africanum* extract in patients with benign prostatic hyperplasia: a randomized, double-blind study, with long-term open label extension. Urology 1999; 54: 473-8.

All prior art reports on clinical usefulness of *pygeum* are based on *pygeum* extracted from the bark of *Prunus africana*. There are no reports in prior art on *pygeum* extracted from a 'renewable resource' such as pruned stem cuttings/twigs of *Prunus domestica* as described in the present invention.

Dosages of *Pygeum* Extract

The accepted form of *pygeum* used in Europe for treatment of BPH is a lipophilic extract of *Prunus africana* standardized to 13% total sterols (typically calculated as beta-sitosterol). Men with mild to moderate BPH sometimes take 50-100 mg two times per day. A double-blind trial found that 100 mg once daily was as effective as 50 mg twice per day. *Pygeum* should be monitored over at least a six-month period to determine efficacy. Men with BPH who are using *pygeum* should be supervised by a doctor. *Pygeum* has been studied in clinical trials for benign prostatic hypertrophy at daily doses of 25 to 200 mg. It is available as standardized preparations Tadenan and Pigenil. Both are in capsule form and contain 50 mg of *Prunus africana* extract (*pygeum*). Recommended dosage is twice daily.

Mechanism of Action of *Pygeum* Extract

The mechanism of action of *pygeum* is described in detail at the following web link: (http://www.evitamins.com/encyclopedia/assets/nutritional-supplement/pygeum/how-it-works). Briefly, chemical analysis and pharmacological studies have confirmed that lipophilic extract of *pygeum* bark has two categories of active constituents:
1) Phytosterols, including beta-sitosterol: These exert anti-inflammatory effects by interfering with the formation of hormone-like substances in the body (prostaglandins) that tend to accumulate in the prostate of men with benign prostatic hyperplasia (BPH).
2) Ferulic esters: These indirectly control testosterone activity in the prostate, which may reduce the risk of BPH.

As per the United States Pharmacoipia, *pygeum* from *Prunus afrincanum* has a 2 active ingredients-β-sito sterols and docosyl ferulate.

The oral intake of natural *pygeum* provides relief by reduction of the enlarged prostate gland and same has been in use for considerable time (Andro M-C, Riffaud J-P. *Pygeum africanum* extract for the treatment of patients with benign prostatic hyperplasia: A review of 25 years of published experience. *Curr Ther Res* 1995(56): 796). Owing to demonstrated usefulness in patients of enlarged prostate, *pygeum* has considerable therapeutic importance and also commercial value. In fact in France, *Pygeum africanum* extract (PAE) has become the primary course of treatment for enlarged prostate.

Challenges in *Pygeum* Production

The Problem

Limited supply of raw material, owing to extraction from a 'non-renewable' source i.e. bark of plant, which results in death of the plant. This has led to environmental concerns and the plant '*Prunus africana*' has been declared an endangered species.

Despite its usefulness, the supply of *pygeum* has been diminishing over the years. Recently, the plant from which it is extracted viz. "*Prunus africana*" has been placed in the list of endangered plants by CITES (Convention On International Trade In Endangered Species Of Wild Fauna & Flora). *Pygeum* is extracted from bark of the plant which naturally results in 'death' of the plant, thus endangering the plant.

The Innovative Solution

New process based on a 'renewable source' leading to 'unlimited supply' of raw material. The new process does not lead to death of plant but yields *pygeum* of same quality (in terms of analytical profile and biological activity) as that obtained from prior art process, in which 'non-renewable' source i.e. bark is used and plant dies.

Concerned at the diminishing supply of *pygeum*, the inventor of the present patent application started exploring other methods/sources of *pygeum*. After considerable research and exploratory activity, it was surprisingly found that large quantities of '*pygeum*' could be extracted from the pruned stem cuttings/twigs of *Prunus domestica* also called the Plum Tree, instead of the bark. For proper growth of the tree, pruning or 'selected cutting' of the superfluous branches is necessary. These cuttings constitute a 'waste plant product' and can be used as a rich source of *pygeum* in the process of the present invention.

None of the prior art studies have indicated extraction of '*pygeum*' from *Prunus domestica* and that too from a 'waste plant product' i.e. pruned stem cuttings/twigs. Nearly all the commercially available preparations have been obtained from the bark of *Prunus africana* which is a 'non-renewable' source. In contrast, the method of the present invention is based upon a 'renewable' source i.e. stem cuttings. Further, the source is a 'waste' plant product' obtained during a normal seasonal activity i.e. pruning.

The novelty, inventive step and industrial application of the present invention (improved process for *pygeum* extraction) is discussed below. The same is purely for illustrative purposes, to promote better understanding of the invention in a simplified and easy manner and should by no means be considered limiting to the description below or in any other manner whatsoever:

Novelty:

Disclosure of a New Process for Extraction of *Pygeum* from a 'Renewable Source' Instead of 'Non-Renewable' Source The method of the present invention is based upon use of a 'renewable' source for extraction of *pygeum* i.e. pruned stem cuttings/twigs obtained during the 'pruning process' of the plant. Since, the plant part used in the herb under present invention is 'pruned stem cuttings' instead of bark, it doesn't destroy the whole plant & therefore, the same plant can be used repeatedly. Further, the source of *pygeum* is a 'waste plant product' i.e. Pruned stem cuttings obtained during regular pruning of the plant *Prunus domestica*. Such a method for extraction of *pygeum* utilizing a waste plant product i.e. pruned stem cuttings/twigs of the plant *Prunus domestica* has not been reported in the prior art. All the prior art methods are based on extraction of *pygeum* from the bark of *Pygeum africanum* (also called *Prunus africana*) and none discloses a method based on 'pruned stem cuttings of *Prunus domestica*'.

Inventive Step:

Development of a New Process for Extraction of *Pygeum* from a 'Renewable Source' Instead of 'Non-Renewable' Source and Demonstration that *Pygeum* Extracted by New Process has Comparable Biological Activity with *Pygeum* Obtained from 'Non-Renewable' Source and is Non-Toxic.

Thus, inventive step of the present invention lies in development of a new process for extraction/production of *pygeum*, which is much more 'eco-friendly' since it involves extraction of *pygeum* from a 'renewable' source instead of 'non-renewable' source.

In new process, there is replacement of a non-renewable source of *pygeum* i.e. tree bark with a renewable source i.e. pruned stem cuttings/twigs. The existing process uses bark of the plant *Prunus africana* which has led to depletion of plant and it being classified as 'endangered species'. In contrast, the new process uses a renewable source of *pygeum* viz.

pruned stem cuttings/twigs of the plant *Prunus domestica*. This doesn't destroy the whole plant & therefore, the same plant can be used repeatedly.

Further the inventors have demonstrated by detailed scientific and analytical studies that the *pygeum* extract obtained by prior art method using 'non-renewable' source (bark of the *Prunus africana* tree) is almost identical to that obtained by the method of the present invention using 'renewable source' ('pruned stem cuttings/twigs of the plant *Prunus domestica* instead of bark) in terms of composition as well as biological effects (prostate gland reduction). Further it is non-toxic.

INDUSTRIAL APPLICATION

The extract is used to make pharmaceutical compositions for the treatment of enlarged prostate. Current pharmaceutical compositions of *pygeum* extract are available in dosage forms (capsules) of 50 mg and 100 mg.

Owing to demonstrated usefulness in patients of enlarged prostate, *pygeum* has considerable therapeutic importance and also commercial value. In fact in France, *Pygeum africanum* extract (PAE) has become the primary course of treatment for enlarged prostate. The method of the present invention has industrial application as it can be carried out at 'commercial scale' owing to easy, long-term and sustainable availability of the plant raw material (pruned stem cuttings) in adequate quantities. The yield of *pygeum* by new method of present invention is found to be more than that obtained from the prior art method based on extraction from bark of *Pygeum africanum* (10 g per kg by new process vs 5-6 g per kg by prior art method).

Further, scientific effort in terms of detailed analytical studies and also pre-clinical studies in rats, has demonstrated equivalence of '*pygeum*' by new process with that of '*pygeum*' obtained by prior art method. This scientific effort forms the basis of acceptance of the *pygeum* obtained by the new process. In absence of proof regarding similarity of composition, safety and also biological activity, *pygeum* obtained by the new process would not have found acceptability at industrial level or approval by authorities regulating use of natural products for therapeutic applications.

OBJECTS OF THE INVENTION

It is an object of the invention to disclose an improved process for the extraction of *pygeum* from a 'renewable plant source' instead of a 'non-renewable plant source'.

Another object of the invention is to disclose an eco-friendly process for the extraction of *pygeum*, which does not lead to 'death' of the plant from which extract is made.

A further object of the invention is to disclose an improved process for the extraction of *pygeum* from *Prunus domestica* (*Indian Plum*) using a renewable plant part i.e. twigs instead of bark.

One more object of the invention is to disclose that the *pygeum* obtained by the new process, utilizing 'renewable plant source' has comparable biological activity and composition as compared to *pygeum* obtained from 'non-renewable' plant source i.e. bark of *Prunus africana*.

Yet another object is to disclose the equivalence of *pygeum* obtained from a renewable source i.e. prunings, with that obtained from a 'non-renewable source' i.e. bark, in terms of composition and biological activity.

Still one more object is to disclose that *pygeum* obtained from a renewable source i.e. prunings or stem cuttings has the same pharmacopeia ingredients as *pygeum* obtained from non-renewable source.

DETAILED DESCRIPTION OF THE INVENTION

The extraction of *pygeum* by the method of the present invention is now described in detail and comprises the following steps:
1. Propagation of plant material
2. Collection of renewable plant part from which *pygeum* is extracted
3. Cleaning and drying of the plant material
4. Pulverizing and reducing the material to powdered form
5. Extraction with organic solvents
6. Concentration and drying to yield final product
7. Analysis and standardization of the final product Details of each step are now described as below:
1. Propagation of the plant material: A specific variety of *Prunus domestica* is propagated on farmland to ensure adequate availability of the raw plant material, without depletion of existing natural resources or endangering existing plant in any manner. The growth cycle of the plant is quite short i.e. only 18-24 months, which makes the process commercially viable in terms of availability of the raw material source (pruned, stem cuttings) in adequate quantities and on long-term, sustainable basis.
2. Collection of specific part from which *pygeum* is extracted: *Pygeum* is extracted from the pruned stem cuttings/twigs of *Prunus domestica* (*Indian Prunus*) generated during the pruning process which is carried out normally every year in autumn, for healthy growth of plant and maximum yield of fruit. Thus, the material used for extraction is a 'plant waste'. The pruned stem cuttings/twigs used for the extraction process are in size range of six inches to eighteen inches and are devoid of leaves.
3. Drying of plant material: The twigs are air-dried in the sun for a period of 10-15 days or more till the moisture content is around 10-12%.
4. Pulverizing: The dried plant material is then cleaned manually and subjected to pulverization in a pulverizer.
5. Extraction with organic solvents: The powdered stem material is extracted four times with chlorinated organic solvent (1:4 volume of solvent) at 35-40° C., each extraction for 2 hours. Solvents which were found to be suitable were methylene dichloride (MDC), chloroform and methanol/water mixture (80:20 v/v). MDC gives best yields.
6. Concentration and drying to yield final product: Once the final product is obtained, the same is subjected to concentration and drying. The extracts are filtered and evaporated under vacuum at 30° C. resulting in concentration of the extract. The final product obtained is a soft dark green mass with bitter almond smell. The yield is about 10 grams per kg having total sterols 15-18% (typically calculated as beta-sitosterol). In contrast, the reported yield from *Pygeum africanum* (also called *Prunus africana*) is 5-6 grams per kg having beta sitosterol content 13-15%. The *pygeum* obtained by method of present invention is thus more in quantity, better in quality and also more economical owing to higher yield and also use of a much cheaper, easily renewable resource i.e. stem cuttings rather than the non-renewable resource i.e. 'bark'.
7. Analysis: The lipophilic extract of *pygeum* bark has 2 categories of active constituents—Phytosterols, including beta-sitosterol and Ferulic esters. Apart from quantitative comparative studies of the ingredients, detailed analytical fingerprinting using High Performance Liquid Chromatography was also carried out. Detailed comparative analysis of *Pygeum* obtained from method of new invention (based on renewable source ie. Prunings/stem cuttings of *Prunus domestica*) and that obtained by prior art method (based on non-renewable source i.e. bark of *Prunus africana*) indicated considerable similarity between the two. Results are given below in Table 1 and Table 2.

TABLE 1

Active constituents of Pygeum from
*Prunus africana* vs *Prunus domestica*

| Pygeum Sample | β-Sitosterol content in dried bark/twigs (mg/g) | Docosyl ferulate content (mg/g) |
| --- | --- | --- |
| *Prunus Africana* (dried bark) | 0.283 | 0.003 |
| *Prunus domestica* (dried twigs) | 0.431 | 0.016 |

The method was validated as per ICH guidelines using dried powdered bark of *Prunus africana* with respect to accuracy, precision, specificity, linearity, range, detection limit, quantitation limit and robustness of the method used. The values were found to be within specified limits.

Thin Layer Chromatographic Profiling

The TLC fingerprint profile of extract from bark of *Prunus africana* and extract from twigs of *Prunus domestica* showed close similarity under UV light and also after derivatization with anisaldehyde-sulphuric acid. The derivatized track of *Prunus africana* showed 13 components and 12 of them were present in the extract of *Prunus domestica* which indicated 92.3 percent matching. The quantitative finger-print comparison of *Prunus africana* and *Prunus domestica* was done through densitometric scans taken at 200 nm (before derivatization) and at 660 nm (after derivatization).

The quantitative comparison of HPLC fingerprints of *Prunus africana* and *Prunus domestica* (giving equi-weightage to all components), showed 89.6 percent matching of two species. Thus, there is considerable chemical similarity between *pygeum* extracted from the dried bark of *Prunus Africana* and that obtained from the dried twigs of *Prunus domestica*.

TABLE 2

Chemical/analytical similarity of *Prunus africana*
vs *Prunus domestica*

| Extract | Anisaldehyde-sulphuric acid derivatives | Quantitiative densitometric scan matching |
| --- | --- | --- |
| *Prunus Africana* (dried bark) | 13 derivatives | 89.6% matching |
| *Prunus domestica* (dried twigs) | 12 matching derivatives (92.3% matching) | |

EXAMPLES

The following examples are given by way of illustration only and describe the innovative process of the present invention. They are by no means restrictive and include embodiments that may be carried out by a person skilled in the art.

Example 1

Laboratory Scale Extraction 100 grams of finely ground powder of *Prunus domestica* twigs (leaves removed) was extracted three times with 200 ml of a methanol/water mixture (80:20 v/v). The extracts were filtered and evaporated under vacuum at 30° C. There was obtained a pasty, soft dark green mass with bitter almond smell. Use of chloroform as the extraction solvent in place of the methanol/water mixture did not give good quality. Use of MDC as the extraction solvent gave best quality & yield of the extract. The presence of sterols in the extract was shown by conventional sterol-detecting reactions.

Example 2

Commercial Scale Extraction

About 800 kg of powdered *Prunus domestica* stem cuttings (leaves removed) were extracted with MDC (methylene dichloride) using 3-4 times the volume of the solvent. Temperature was raised to 30-35 degree Celsius for 3-4 hours and stirring carried out. Thereafter MDC was transferred from the rotary extractor to distillation unit of kilo liter capacity. Powder was extracted 3 times. Solvent was evaporated and concentration carried out till volume was considerably reduced and a gummy mass was obtained. This mass is referred to as '*pygeum*'.

Biological Activity and Safety of *Pygeum* Obtained by New Process

Biological Activity

The biological activity of *pygeum* obtained by the new process of the present invention was tested by its effect on reduction of enlarged prostate gland in test animals (Testosterone—Induced Benign Prostatic Hyperplasia in Wistar Rats).

Study Plan:

The animals were randomly allocated to eight different groups (n=10/group), prior to initiation of treatment. Each group was divided into two sets of 5 animals each. Test Item and Reference item formulations were prepared in Rice bran oil freshly, at the time of dosing. Inducing agent (Testosterone propionate) was prepared in Corn oil. The test item and reference item were administered orally, daily. The vehicle control was administered orally and subcutaneously. The inducing agent was administered subcutaneously. Dose volume was maintained at 2 ml/kg body weight for oral and 1 ml/kg for subcutaneous administration, throughout the treatment period. Clinical signs/symptoms were observed daily after dosing. Mortality was recorded twice a day. Detailed clinical examination was done on days 1, 7, 14, 21, 28 and 35. Animals were weighed on the day of randomization and during the days 1, 8, 14, 22, 29 and 35 of treatment period. Additionally body weights were recorded on the days of scheduled necropsy to calculate relative organ weight. Feed intake per animal (g/day) was calculated using amount of feed given and leftover by each cage on weekly basis. Weekly measurements and recording of water consumption and Urine output of all experimental animals were done. Animals were fasted overnight prior to blood collection. Blood samples were collected for haematology, urinalysis and clinical chemistry analysis on days 15 (interim sacrifice) and 36 (terminal sacrifice) before necropsy. On days 15 and 36, all animals of set I and set II respectively, were subjected to necropsy and detailed gross pathological evaluation. All protocol listed tissues from all groups were processed following standard histostaining technique procedure and were evaluated microscopically by study pathologist.

Results:

Activity of 'test compound' (*pygeum* obtained by new process using 'renewable' resource), in reducing testosterone—induced benign prostatic hyperplasia in male wistar rats was comparable to that of 'reference compound' (*pygeum* obtained by prior art process using 'non-renewable' resource) at dose levels of 100 and 200 mg/kg body weight, in male wistar rat.

Safety

Safety aspects of *pygeum* obtained by the new process were evaluated using standard toxicity test protocols—Acute (oral 2000 mg/Kg body weight for 14 days) and sub-chronic (dose levels of 25 mg/Kg, 50 mg/Kg and 100 mg/Kg in the dose volume of 1 ml/100 g body weight given daily for 28 days). Toxicity studies were carried out independently in mice and rats. Results indicated that the *pygeum* obtained by the new process was non-toxic.

CONCLUDING REMARKS

The prior art process suffers from the disadvantage of very limited raw material source i.e. bark of the tree *Prunus africanum* owing to a ban on its export. "*Prunus africanum*" has been placed in the list of endangered plants by CITES (Convention On International Trade In Endangered Species Of Wild Fauna & Flora). *Pygeum* is extracted from bark of the plant which naturally results in 'death' of the plant, thus endangering the plant.

However, in the new process, there is no such limitation because bark is not used as the raw material source. Instead, prunes and twigs obtained during routine pruning of the plants are used for extraction in the process of the present invention. Thus, the new process offers significant technical advantages in terms of economy and eco-friendliness, being based on a 'renewable source' of raw material.

The process of the present invention offers significant commercial advantage in terms of production because the plant source used is a cheap, bio-waste i.e. twigs and prunes obtained during routine pruning of the plant. The bio-waste obtained can be easily dried and stored to serve as a valuable raw material and eco-friendly source for extraction of *pygeum*.

The *pygeum* obtained by the process of the present invention is not only similar in chemical composition but also biological activity as compared to the *pygeum* obtained from 'non-renewable plant source'. It can be easily formulated into health supplements, pharmaceutical formulations. The concentration of total sterols in *pygeum*, typically calculated as beta-sitosterol is standardized as per existing pharmacopeia standards for product use. As innovations in extraction technology and also analytical methods take place, there is strong possibility of more potent and chemically defined extracts of *pygeum*, for the treatment of BPH (Benign Prostatic Hyperplasia). This may lead to revision of pharmacopeia standards as per dosages standardized for therapeutic effects and mode of product use e.g. as medicine or as health supplements/dietary supplements in form of functional food product or drink.

We claim:

1. A commercially viable process using biowaste for the extraction of *pygeum* from *Prunus domestica* (*Indian prunus*) comprising the steps of:
    collecting stem cuttings/twigs with leaves removed from the *Prunus domestica*, to produce a first product;
    drying the first product until the moisture content of the first product is about 10-15%, to produce a dried first product;
    powdering the dried first product by pulverization, to produce a powdered product;
    treating the powdered product with a chlorinated organic solvent at 35-40° C., to produce an extract; and
    filtering and drying the extract under vacuum at 30° C. to obtain *pygeum* as a greenish mass with bitter almond smell containing beta-sitosterol therein and in which the concentration of the beta-sitosterol is 15-18% by weight of the *pygeum* and wherein the *pygeum* has anti-BPH activity.

2. The process of claim 1 wherein the chlorinated organic solvent used in the extraction process is methylene dichloride (MDC).

* * * * *